United States Patent [19]

Loewe et al.

[11] Patent Number: 5,037,974

[45] Date of Patent: Aug. 6, 1991

[54] CYCLIZATION PROCESS FOR SYNTHESIS OF A BETA-LACTAM CARBAPENEM INTERMEDIATE

[75] Inventors: Mallory F. Loewe, Marlboro; Raymond Cvetovich, Scotch Plains; George G. Hazen, Perth Amboy, all of N.J.

[73] Assignee: Merck & Co., Inc., Rahway, N.J.

[21] Appl. No.: 568,649

[22] Filed: Aug. 14, 1990

Related U.S. Application Data

[63] Continuation of Ser. No. 507,016, Apr. 10, 1990, abandoned, which is a continuation of Ser. No. 197,552, May 23, 1988, abandoned.

[51] Int. Cl.$^5$ .................. C07D 205/08; C07B 43/06
[52] U.S. Cl. ..................................................... 540/200
[58] Field of Search ........................................ 540/200

[56] References Cited

U.S. PATENT DOCUMENTS 4,360,684 11/1982 Cvetovich ........................ 549/291
4,581,170 4/1986 Mueller ............................ 540/355

FOREIGN PATENT DOCUMENTS 0051234 6/1982 European Pat. Off. ............ 540/200

OTHER PUBLICATIONS

Y. Watanabe et al., Chemistry Letters, pp. 443–444, 1981.
H. Huang et al., Chemistry Letters, pp. 1465–1466, 1984.
M. Ohno et al., J. Am. Chem. Soc., vol. 103, 1981, pp. 2405–2406.
D. G. Melillo et al., Tetrahedron Letters, vol. 21, pp. 2783–2786, 1980.
T. Kametani et al., J. Am. Chem. Soc., vol. 102, pp. 2060–2065.
L. Birkofer et al., Liebig's Analen Chem., 1975, pp. 2195–2200.
D. G. Melillo et al., J. Org. Chem., 1986, 51, pp. 1498–1504.
T. Mukaiyama et al., Tetrahedron Letters, No. 22, pp. 1901–1904.

*Primary Examiner*—Mark L. Berch
*Attorney, Agent, or Firm*—Frank P. Grassler; Robert J. North; Hesna J. Pfeiffer

[57] ABSTRACT

A process is described for the synthesis of 3(S)-4(R)-3-[1(S)-hydroxyethyl]-4-(alkoxycarbonylmethyl)-azetidin-2-one (II) which is a useful intermediate in the synthesis of carbapenem antibiotics.

9 Claims, No Drawings

CYCLIZATION PROCESS FOR SYNTHESIS OF A BETA-LACTAM CARBAPENEM INTERMEDIATE

This is a continuation of application Ser. No. 07/507,016, filed Apr. 10, 1990, now abandoned, which was a continuation of application Ser. No. 07/197,552, filed May 23, 1988, now abandoned.

BACKGROUND OF THE INVENTION

1) Field of the Invention

This invention relates to a process for producing a beta-lactam intermediate having desired chirality which is essential in carbapenem synthesis.

2) Brief Description of Disclosures in the Art

Carbapenem antibiotics, particularly thienamycin and imipenem (see U.S. Pat. Nos. 3,950,377 and 4,194,047) are well known for treating a broad spectrum of gram-negative and gram-positive bacterial infections.

Processes for synthesis of these type antibacterial agents are well known in the art as witness the following Patents issued inter alia to Merck & Co.; U.S. Pat. Nos. 4,543,257, 4,234,596, 4,360,684 and 4,232,030.

In order to develop, faster, less expensive and better methods for their production, research is continually being carried out in this area. One focus in this field has been on different modes for the synthesis of the starting azetidinone intermediate II, 3(S)-4(R)-3-[1(S)-hydroxyethyl]-4-(alkoxycarbonylmethyl)-azetidin-2-one.

One particular aspect is in the development of an efficient, convenient and inexpensive route to convert beta amino acid I, [2S-[2R*,(R*),3S*]]-3-amino-2-(1-hydroxyethyl)pentanedioic acid 5-methyl ester, (CAS Registry No. 79814-47-4), by suitable ring closure to beta lactam II, as seen by the following process sequence,

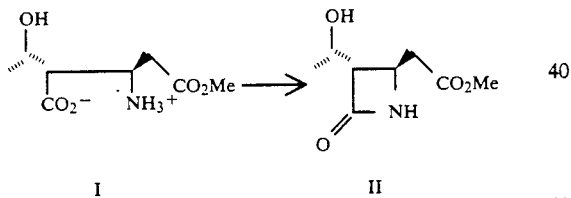

The ring closure, i.e. cyclodehydration, of I to II, can be effected by using the prior art procedures of: H. Huang et al. in *Chem. Letters*, p. 1465 (1984) utilizing 2-chloro-1-methylpyridinium iodide; M. Ohno et al. in *JACS*, 103, p. 2406 (1981) using pyridine disulfide/triphenyl phosphine; D. Melillo et al. in *Tet. Letters*, p. 2783 (1980) and T. Kametani et al, in *JACS*, 102, p. 2060 (1980) using dicyclohexyldiimide; M. Ohno et al. in EPA Publication No. 0051234 (1982) using a heterocyclic disulfide, triphenylphosphine in the presence of an alkyl nitrile; and L. Biokofer et al, in *Liebig's Ann. Chem.*, p.2195 (1975) using the Grignard reaction on the amino-ester. Earlier disclosures also include T. Mukaiyama et al. in *Tet. Letters*, 22. p. 1901–1904 (1970) which describe peptide synthesis utilizing 2,2′-pyridyl-disulfide as an oxidant.

However, these reagents are very expensive especially when utilized on a plant scale.

A beta-lactam ring closure procedure has been reported by Y. Watanabe et al., Chem. Letters 1981, pp. 443–444, which employs a two phase liquid-liquid phase transfer system of methylene chloride/H2O, tetrabutylammonium hydrogen sulfate as the phase transfer agent, and methanesulfonyl chloride, potassium bicarbonate as the ring closure agents. However, this system gives poor yields of II from I, primarily due to the instability of I in the basic aqueous phase.

What is desired is an improved process for the ring closure of I to II, which can be carried out efficiently on a large scale, eliminating the use of expensive reagents and aqueous phase systems, to obtain high yields of product II.

SUMMARY OF THE INVENTION

It has been found that by carrying out the ring closure of I to II, in an organic solvent, e.g. acetonitrile, using methanesulfonyl chloride and sodium bicarbonate as the ring closure agents, compound II can be obtained in substantially pure form, in high yield, and on a large scale.

In accordance with this invention there is provided a process comprising the step of: 1) contacting

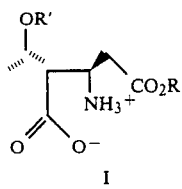

with methanesulfonyl chloride and sodium bicarbonate in a non-interfering organic solvent at a temperature in the range of 0° to 100° C., for a sufficient time to produce:

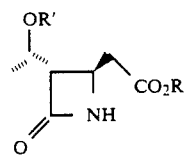

wherein R and R′ are defined hereinbelow.

BRIEF DESCRIPTION OF THE INVENTION AND PREFERRED EMBODIMENTS

The invention process involves the formation of beta-lactam ester II from the beta-amino acid I. Values of R ester radical include: $C_1$–$C_6$ linear and branched alkyl, including methyl, ethyl, propyl, isopropyl, n-butyl, sec-butyl, t-butyl, pentyl, isopentyl, n-hexyl, isohexyl, and the like; benzyl and phenyl; which radicals can be substituted with substituents non-interfering with the ring closure under the reaction conditions including halo, nitro, $C_1$–$C_4$ alkoxy, e.g. chloro, bromo, methoxy, and the like. Preferred R group is methyl.

Values of R′ include: hydrogen, triorganosilyl, wherein the term "organo" group includes $C_1$–$C_6$ linear or branched alkyl, benzyl and phenyl; $C_1$–$C_6$ linear or branched alkylsulfonyl; phenylsulfonyl; formyl; and $C_1$–$C_6$ linear or branched acyl; which groups can be substituted by substituents inert under the reaction conditions.

The $C_1$–$C_6$ linear or branched alkyl, wherein the alkyl is also included in the alkylsulfo, include methyl, ethyl, propyl, isopropyl, n-butyl, isobutyl, sec-butyl, t-butyl, pentyl, isopentyl, n-hexyl, isohexyl and the like.

Substituents which can be present on the above-described R′ groups, include i.e. $C_1$–$C_4$ alkyl, benzyl and particularly on the phenyl groups include, halo, i.e. chloro, fluoro, bromo; nitro, $C_1$-$C_4$ alkoxy, i.e. methoxy, ethoxy, isopropoxy, t-butoxy; trifluoromethyl, and the like. Preferred R' substituent is hydrogen.

The solvent for the process step is an organic solvent in which I is relatively insoluble and II is relatively soluble, and which does not adversely interfere with the ring closure. By the term "relatively insoluble" is meant that a sufficient amount of the compound I is soluble to enable a solution process to occur. Representative classes include a cyclic or acyclic $C_2$-$C_{10}$ ether including linear alkyl, branched alkyl, cycloalkyl, including tetrahydrofuran (THF), diethylether, dipropylether, dioxane, dimethoxyethane; $C_1$-$C_6$ alkyl nitrile, including propionitrile and acetonitrile; and a $C_{1-4}$ linear or branched alcohol, including propanol, isopropanol, and the like. Preferred solvents are acetonitrile, isopropanol and propanol.

The starting material I is known in the art (see U.S. Pat. No. 4,360,684, structure 23, hereby incorporated by reference).

In the process, compound I is contacted with the solution of methanesulfonyl chloride and solid sodium bicarbonate in an organic solvent to effect ring closure. Since I is relatively insoluble in the solvent, it can be added all at once, in portions, in a batchwise or continuous manner, or as a slurry. Generally 1 to 50 ml of solvent per gram of I is utilized, but larger quantities can also be successfully utilized. Preferred is where I is added in portions to a suspension of $NaHCO_3$, and a solution of methanesulfonyl chloride in the solvent. The amount of methanesulfonyl chloride (MSC) used is generally in a 1 to 3:1 molar ratio of MSC:I and preferably a 1.05:1 MSC:I molar ratio.

The sodium bicarbonate is present in an amount of from a 2 to 12:1 molar ratio to I and preferably a 5 to 6:1 molar ratio, such that an excess is present. Higher amounts than described can be used but are not necessary.

The process is generally conducted in an initial range of from 0° to 100° C., preferably 20° to 60° C., and particularly preferred 45°–50° C., and allowed to stir for a sufficient time, e.g., 2–24 hours, to allow complete ring closure to occur. After stirring, the reaction mixture is cooled, e.g. to 0°–5° C., and filtered to allow separation of inorganic salts.

Pressure in the process is preferably atmospheric but slightly lower (reduced) and higher pressures can also be successfully employed.

The compound II is collected, for example, by evaporation of the solvent until crystallization of II occurs, filtered, washed and dried. The purity of II thus obtained is about 98%. II can be further purified by recrystallization from ethyl acetate/hexane. Yields of II are generally in the range of 89 to 97% of theory calculated on starting I, when using preferred ranges of methanesulfonyl chloride agent (5% excess) and sodium bicarbonate (600% excess).

II can be used directly in carbapenem antibiotic synthesis as seen in U.S. Pat. No. 4,290,947, hereby incorporated by reference for that purpose.

The following examples are illustrative of the invention and should not be construed as being limitations on the scope or spirit thereof.

EXAMPLE 1

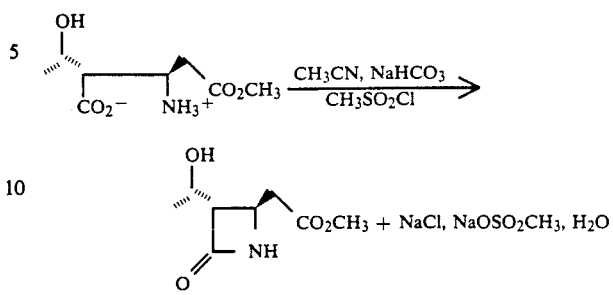

(15.4 gm, 183 mmol) $NaHCO_3$ was suspended in 150 ml $CH_3CN$ containing (3.6 g, 30.9 mmol) $CH_3SO_2Cl$ and warmed to and maintained at 55° C. Solid I (6.25 g, 30.1 mmol) was added over 1–2 hours. After a 4-hour period, the reaction was cooled to 5° C. and the inorganic salts were filtered, leaving II in 97% yield as determined by high pressure liquid chromatography, as an acetonitrile solution. The main impurity was the mesylate of II:

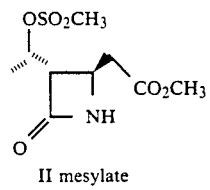

II mesylate

EXAMPLE 2

A vigorously stirred suspension of 200 kg $NaHCO_3$ (U.S. patent) in acetonitrile (1194L) was heated to 43° C. Methanesulfonyl chloride (47.5 kg) was added and heating was continued to 47° C. To this suspension was continuously added a slurry of I (77.5 kg) in acetonitrile (635L) over a 2 hr period, followed by an acetonitrile (207L) rinse. The resulting suspension was vigorously stirred at 47°–49° C. for 2.5 hr until all the methanesulfonyl chloride had been consumed (HPLC analysis).

The reaction vessel was cooled to 3° C. and the contents filtered through a frame press to remove the reaction solids. The solids were rinsed with cold (3° C.) acetonitrile and the filtrates combined (3160L). An HPLC analytical assay of the II/acetonitrile filtrate solution yielded 66.6 kg II in 3160L acetonitrile, a 94.1% yield of II.

EXAMPLE 3

To a stirring suspension of $NaHCO_3$ (2.5 gm, 30 mmol) in dry isopropyl alcohol (25 mL) was added methanesulfonyl chloride (0.600 gm, 5.25 mmol). The suspension was heated to 45° C. I (1.03 gm, 5.0 mmol) was added in 4 portions over 1 hour. The suspension was stirred for 5.5 hr until no methanesulfonyl chloride remained (HPLC analysis). The reaction was cooled to 2° C. and filtered. The solids were washed with cold IPA and the filtrates combined. HPLC analytical assay of the isopropanol (IPA) solution yielded 0.694 gm of II (74% yield).

COMPARATIVE EXAMPLE

The following are details of Watanabe's procedure as applied to the conversion of I to II showing low yield.

Liquid-Liquid Phase Transfer Reaction

To a 10 ml flask containing amino acid I (0.20 gm, 1.0 mmol), KHCO$_3$ (0.40 gm, 4.0 mmol) in 1.5 ml H$_2$O under N$_2$ atmosphere with stirring was added a methylene chloride (5.0 ml) solution of methanesulfonyl chloride (0.23 gm, 2.0 mmol). The two phase system was vigorously stirred at room temperature. A TLC (silica gel/EtOAc) at 1.5 hr of the organic phase contained several spots, one corresponding to the β-lactam (co-spot). After 18 hr the organic soluble material was isolated and contained the desired β-lactam II in 32% yield. The aqueous phase contained hydrolysed starting I (β-amino diacid).

What is claimed is:

1. A process carried out in a single liquid phase, comprising the step of contacting:

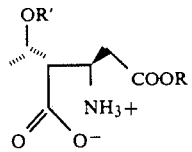   I with methanesulfonyl chloride and sodium bicarbonate in an organic solvent, at a temperature in the range of 0° to 100° C., for a sufficient time to produce:

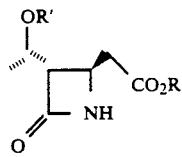   II where R is C$_1$–C$_6$ linear and branched alkyl, benzyl or phenyl, which can be substituted with non-interfering substituents under the reaction conditions and R' is C$_1$–C$_6$ linear or branched alkyl, benzyl and phenyl, C$_1$–C$_6$ linear or branched alkylsulfonyl; phenylsulfonyl; or C$_1$–C$_6$ linear or branched acyl; which groups can be substituted by other non-interfering substituents under the reaction conditions.

2. The process of claim 1 wherein structure I said R is C$_1$–C$_4$ linear or branched alkyl.

3. The process of claim 2 wherein Structure I said R is methyl.

4. The process of claim 1 wherein said R' is hydrogen.

5. The process of claim 1 wherein temperature is conducted at 20° to 60° C.

6. The process of claim 1 wherein said solvent for the process step is an organic solvent, selected from the group consisting of a cyclic or acyclic C$_2$–C$_{10}$ linear alkyl or branched alkyl ether; C$_1$–C$_6$ alkyl nitrile; and a C$_{1-4}$ linear or branched alcohol.

7. The process of claim 6 wherein said solvent is acetonitrile, isopropanol or propanol.

8. The process as claimed in claim 1, wherein said temperature range is 40°–55° C.

9. The process as claimed in claim 1, wherein said organic solvent is acetonitrile.

* * * * *